United States Patent
Picard-Lesboueyries

(10) Patent No.: US 6,878,367 B2
(45) Date of Patent: Apr. 12, 2005

(54) COMPOSITIONS COMPRISING A SAPOGENIN AND A XANTHINE AND METHODS OF USING THE SAME

(75) Inventor: Elisabeth Picard-Lesboueyries, Velizy (FR)

(73) Assignee: L'Oreal, Paris (FR)

(*) Notice: Subject to any disclaimer, the term of this patent is extended or adjusted under 35 U.S.C. 154(b) by 15 days.

(21) Appl. No.: 09/933,742

(22) Filed: Aug. 22, 2001

(65) Prior Publication Data

US 2002/0054928 A1 May 9, 2002

(30) Foreign Application Priority Data

Aug. 22, 2000 (FR) .............................................. 00 10805

(51) Int. Cl.⁷ ................................................. A61K 7/06
(52) U.S. Cl. ........................ 424/70.1; 424/401; 424/400
(58) Field of Search ............................... 424/70.1, 400, 424/401

(56) References Cited

U.S. PATENT DOCUMENTS

| 3,136,761 A | * | 6/1964 | Loken ................... 260/239.55 |
| 4,288,433 A | * | 9/1981 | Koulbanis et al. .......... 424/232 |
| 4,684,522 A | | 8/1987 | Marissal et al. |
| 5,523,090 A | * | 6/1996 | Znaiden et al. ............. 424/401 |
| 5,770,223 A | * | 6/1998 | Bonte et al. ................ 424/450 |

FOREIGN PATENT DOCUMENTS

| EP | 0 728 472 A2 | 8/1996 |
| FR | 2499405 | 8/1982 |
| FR | 2554344 A1 | 5/1985 |
| FR | WO 00/30603 | 6/2000 |

* cited by examiner

Primary Examiner—Thurman K. Page
Assistant Examiner—Rachel M. Bennett
(74) Attorney, Agent, or Firm—Oblon, Spivak, McClelland, Maier & Neustadt, P.C.

(57) ABSTRACT

Compositions which comprise, in a physiologically acceptable medium, at least one sapogenin or a derivative or natural extract containing the same, and at least one xanthine base are useful, in particular, for preventing or combating cellulite and/or for refining the figure or the contours of the face. Preferably, the composition comprises diosgenin or an extract of wild yam, combined with caffeine.

35 Claims, No Drawings

COMPOSITIONS COMPRISING A SAPOGENIN AND A XANTHINE AND METHODS OF USING THE SAME

CROSS REFERENCES TO RELATED APPLICATIONS

This application claims priority to French Patent Application No. 0010805, filed on Aug. 22, 2000, and which is incorporated herein by reference in its entirety.

BACKGROUND OF THE INVENTION

1. Field of the Invention

The present invention relates to compositions which comprise, in a physiologically acceptable medium, at least one sapogenin chosen from diosgenin and hecogenin, or a derivative or a natural extract containing the same, and at least one xanthine base. The present invention also relates to the use of such compositions.

2. Discussion of the Background

Sapogenins are compounds resulting from the acidic hydrolysis of saponosides, which are themselves heterosides of very high molecular weight present in the plant kingdom. Among the sapogenins which may be mentioned in particular are: diosgenin, hecogenin, smilagenin, sarsapogenin, tigogenin, yamogenin, and yuccagenin.

These compounds have in common a steroidal structure comprising a variable number of hydroxyl and/or oxo substituents and/or a variable number of double bonds. They are known as natural chemical precursors of steroidal hormones and are described, in this respect, as constituents of choice for various cosmetic or pharmaceutical preparations.

Diosgenin, or spirost-5-en-3-beta-ol, can be extracted from fenugreek or from various Dioscorea plants, for example from the root of wild yam. Diosgenin has been described in particular as being usable in slimming compositions, on account of its ability to inhibit the storage of biochemical lipid material in adipose tissue (see, FR-2 786 097).

Cosmetic compositions for promoting epidermal renewal, which combine alfalfa sapogenins with various active agents including xanthine bases, are known from U.S. Pat. No. 5,770,223. These compositions are intended to combat the effects of ageing of the skin and to stimulate restoration of the hair or to prevent hair loss. These sapogenins differ chemically from those present, in particular, in wild yam and agave. Moreover, the compositions obtained in U.S. Pat. No. 5,770,223 are not described as being capable of having a slimming effect.

Thus, there remains a need for compositions which have a slimming effect even when applied topically. There also remains a need for compositions and methods which are effective for preventing and/or combating cellulite and for refining the figure or the contours of the face.

SUMMARY OF THE INVENTION

Accordingly, it is one object of the present invention to provide novel compositions which have a slimming effect.

It is another object of the present invention to provide such novel compositions which are effective even when applied topically.

It is another object of the present invention to provide novel compositions which are useful for preventing or combating cellulite.

It is another object of the present invention to provide such novel compositions which are effective even when applied topically.

It is another object of the present invention to provide novel compositions which are useful for refining the figure or the contours of the face.

It is another object of the present invention to provide such novel compositions which are effective even when applied topically.

It is another object of the present invention to provide novel methods for preventing or combating cellulite.

It is another object of the present invention to provide novel methods for refining the figure or the contours of the face.

These and other objects, which will become apparent during the following detailed description, have been achieved by the inventor's discovery that compositions which comprise, in a physiologically acceptable medium:

(A) at least one sapogenin selected from the group consisting of diosgenin, hecogenin, a derivative or a natural extract containing a sapogenin, and mixtures thereof; and (B) at least one xanthine base or a plant extract containing the same are effective for preventing or combating cellulite and for refining the figure or the contours of the face.

Thus, the present invention has been achieved by the inventor's discovery that combining certain sapogenins with xanthine bases, which are themselves well known in slimming products as inhibitors of phosphodiesterase and/or of lipoprotein lipase, could improve the efficacy of slimming compositions containing these sapogenins.

DETAILED DESCRIPTION OF THE PREFERRED EMBODIMENTS

Thus, in a first embodiment, the present invention provides novel compositions which comprise, in a physiologically acceptable medium:

(A) at least one sapogenin selected from the group consisting of diosgenin, hecogenin, a derivative or a natural extract containing a sapogenin, and mixtures thereof; and (B) at least one xanthine base or a plant extract containing the same.

According to one preferred embodiment, the present invention relates more particularly to compositions in which the sapogenin is diosgenin. Diosgenin may be extracted from Dioscorea tubers by a process comprising, successively: hydrolysis of the heterosides in mineral acid medium (optionally after fermenting and drying the tubers); and filtration of the insoluble fraction, which is then neutralized, washed and treated with an apolar solvent. However, other extraction processes may be used. Diosgenin is also commercially available from the company Sigma under the trade name Diosgenin.

In the context of the present invention, it should be understood that the term "sapogenin derivatives" in particular means sapogenin esters such as hecogenin acetate.

In the context of the present invention, it should also be understood that the expression "natural extracts" means any plant extract containing diosgenin and/or hecogenin, after an optional treatment intended to hydrolyse the saponosides, such as an extract of wild yam rhizome (*Dioscorea villosa* or *Dioscorea mexicana* or *Dioscorea opposita* in particular), which contains diosgenin, or an extract of agave leaves (*Hechtia texensis* in particular) containing hecogenin.

The sapogenin may be present in the composition in an amount of from 0.001% to 10% by weight, preferably from 0.05% to 5% by weight, of the total weight of the composition according to the present invention.

In addition to the sapogenin, this composition also contains at least one xanthine base. Among the xanthine bases which may be used according to the present invention, mention may be made of: caffeine, theophylline, theobromine, acefylline, xanthinol nicotinate, diniprophylline, diprophylline, etamiphylline and its derivatives, etophylline, proxyphylline, pentophylline, propentophylline, pyridophylline, and bamiphylline, without this list being limiting.

It is particularly preferred to use caffeine, theophylline, theobromine, and acefylline. These xanthine bases are known as inhibitors of phosphodiesterase, which is the enzyme responsible for the degradation of cAMP. By increasing the intracellular content of cAMP, these xanthine bases promote lipolytic activity and thus constitute first-rate slimming active agents.

As examples of plant extracts containing xanthine bases, mention may be made in particular of extracts of tea, of coffee, of guarana, of Paraguay tea, and of cola, without this list being limiting.

The xanthine base may be present in the composition in an amount of from 0.01% to 10% by weight, preferably from 0.1% to 7% by weight, of the total weight of the composition according to the present invention.

The composition according to the present invention can be in any pharmaceutical form normally used for topical application to the skin, in particular in the form of an optionally gelified oil-in-water or water-in-oil or multiple emulsion, a silicone emulsion, a microemulsion or nanoemulsion, a pasty or solid liquid anhydrous product, a dispersion of oil in an aqueous phase in the presence of spherules, it being possible for these spherules to be polymer nanoparticles such as nanospheres and nanocapsules or, better still, lipid vesicles of ionic and/or nonionic type.

The present composition may be more or less fluid and may have the appearance of a white or coloured cream, an ointment, a milk, a lotion, a serum, a paste, a mousse or a gel. It can optionally be applied to the skin in the form of an aerosol. It can also be in solid form and, for example, in the form of a stick. It can be used as a care product and/or as a make-up product for the skin.

In a known manner, the composition of the present invention can also contain any of the adjuvants that are common in cosmetics and dermatology, such as hydrophilic or lipophilic gelling agents, hydrophilic or lipophilic active agents, preserving agents, antioxidants, solvents, fragrances, fillers, pigments, hydrophilic screening agents, odor absorbers and colorants. The amounts of these various adjuvants are those conventionally used in the fields under consideration, and, for example, are from 0.01 to 20% by weight of the total weight of the composition. Depending on their nature, these adjuvants can be introduced into the fatty phase, into the aqueous phase, into the lipid vesicles, and/or into the nanoparticles.

When the composition according to the present invention is an emulsion, the proportion of the fatty phase can range from 5% to 80% by weight, preferably from 5% to 50% by weight, of the total weight of the composition.

As fatty substances which can be used in the invention, it is possible to use mineral oils, oils of animal origin, synthetic oils, silicone oils, and fluoro oils. Fatty substances which can also be used include fatty acids, waxes, and gums, and in particular silicone gums.

The emulsifiers and co-emulsifiers optionally used in the present composition in emulsion form are chosen from those used conventionally in the field under consideration. These emulsifiers and co-emulsifiers are preferably present in the composition in a proportion ranging from 0.3% to 30% by weight, preferably from 0.5% to 20% by weight, of the total weight of the composition. As emulsifiers and co-emulsifiers which can be used in the invention, it is particularly advantageous to use esters of a fatty acid and of a polyol, such as PEG-100 stearate, PEG-50 stearate, and PEG-40 stearate; sorbitan tristearate, oxyethylenated sorbitan stearates available under the trade names Tween® 20 or Tween® 60, for example; and mixtures thereof.

Hydrophilic gelling agents which may be mentioned in particular are carboxyvinyl polymers (carbomer), acrylic copolymers such as acrylate/alkyl acrylate copolymers, polyacrylamides, polysaccharides, natural gums, and clays. As lipophilic gelling agents, mention may be made of modified clays such as bentones, metal salts of fatty acids, and hydrophobic silica.

As active agents which complement the action of the slimming active agents according to the present invention, it is possible in particular to use:

active agents which act on the microcirculation (vasoprotectors or vasodilators), such as flavonoids, extracts of Ginkgo biloba, ruscogenins, esculosides, escin extracted from common horsechestnut, nicotinates, hesperidine methyl chalcone, butcher's-broom and essential oils of lavender or of rosemary;

firming active agents and/or anti-glycant active agents (which prevent binding of sugar to collagen fibres), such as extracts of *Centella asiatica* and of St.-Paul's-wort, which stimulate collagen synthesis, silicon, amadorine, vitamin C and its derivatives, and retinol and its derivatives;

and mixtures thereof.

In the event of incompatibility with each other or with the sapogenin, the active agents indicated above and/or the sapogenin can be incorporated into spherules, in particular ionic or nonionic vesicles and/or nanoparticles (nanocapsules and/or nanospheres), so as to isolate them from each other in the composition.

Needless to say, a person skilled in the art will take care to select the optional compounds) to be added to the compositions according to the present invention, as well as the concentration thereof, such that the advantageous properties intrinsically associated with the compositions in accordance with the present invention are not, or are not substantially, adversely affected by the addition envisaged.

The invention also relates to the use of a composition comprising, in a physiologically acceptable medium, at least one sapogenin or a derivative or a natural extract containing the same, and at least one xanthine base or a plant extract containing the same, to prevent or combat cellulite and/or to refine the figure or the contours of the face.

As noted above, the present compositions may be used for preventing and/or combating cellulite by applying the composition to the skin of a subject in need thereof. When using the present composition in such a manner, the composition is suitably applied to the skin in an amount of 0.1 to 10 mg/cm$^2$, preferably 0.5 to 5 mg/cm$^2$, more preferably 1 to 3 mg/cm$^2$ (these numbers being approximate). The amount is generally 2 mg/cm$^2$. The composition may be applied to the skin in a regime which includes application of the composition weekly, every other day, daily, or twice daily. The skin to which the composition is to be applied is not limited but particularly includes the skin of the thighs, face, and upper arms. The application of the composition to the skin may be continued until the desired degree of improvement is achieved or continued indefinitely for preventative purposes.

As also noted above, the present compositions may be used for refining the figure or the contours of the face by applying the composition to the skin of the figure or the skin of the face of a subject in need thereof. When using the present composition in such a manner, the composition is suitably applied to the skin in an amount of 0.1 to 10 mg/cm$^2$, preferably 0.5 to 5 mg/cm$^2$, more preferably 1 to 3 mg/cm$^2$ (these numbers being approximate). The amount is generally 2 mg/cm$^2$. The composition may be applied to the skin in a regime which includes application of the composition weekly, every other day, daily, or twice daily. Once again, the skin to which the composition is to be applied is not limited but particularly includes the skin of the thighs, face, and upper arms. The application of the composition to the skin may be continued until the desired degree of improvement is achieved or continued indefinitely for preventative purposes.

The sapogenin may be chosen in particular from diosgenin, hecogenin, smilagenin, sarsapogenin, tigogenin, yamogenin and yuccagenin. Diosgenin is preferred for these uses.

Other features of the invention will become apparent in the course of the following descriptions of exemplary embodiments which are given for illustration of the invention and are not intended to be limiting thereof.

EXAMPLES

In the following examples, and throughout this specification, all percentages are by weight and based on the total weight of the final composition.

Example 1

Slimming Cream for the Body

| A: | Acrylates/C$_{10-30}$ alkyl acrylate copolymer | 0.5% |
|---|---|---|
|  | Water | 12% |
| B: | Hexyldecanol | 10% |
|  | Isononyl isononanoate | 10% |
|  | Diosgenin | 0.3% |
| C: | Salicylic acid | 2.5% |
|  | Triethanolamine | 4% |
|  | Water | 20% |
|  | Glyercol | 6% |
|  | Caffeine | 3% |
| D: | Polyacrylamide and C$_{13-14}$ isoparaffin and laureth-7 | 0.5% |
| E: | Water | qs |
|  | Alcohol | 15% |

The composition may be prepared in the following manner. The polymer of phase A is dispersed in water with stirring at 40° C. The constituents of phase B are heated until completely dissolved (70° C.), and the temperature is then returned to 40° C. The constituents of phase C are dissolved at 50° C. Phase B is then introduced into phase A with stirring. After checking for the absence of crystals by microscope, phases C, D, and then E are then added to the mixture previously obtained.

Example 2

Slimming Cream for the Body

| A: | Acrylates/C$_{10-30}$ alkyl acrylate copolymer | 0.5% |
|---|---|---|
|  | Water | 12% |
| B: | Hexyldecanol | 10% |
|  | Isononyl isononanoate | 10% |
|  | Extract of wild yam rhizome (Dioscorea villosa) containing 3% diosgenin | 0.3% |
| C: | Salicylic acid | 2.5% |
|  | Triethanolamine | 4% |
|  | Water | 20% |
|  | Glyercol | 6% |
|  | Caffeine | 3% |
| D: | Polyacrylamide and C$_{13-14}$ isoparaffin and laureth-7 | 0.5% |
| E: | Water | qs |
|  | Alcohol | 15% |

The above composition may be prepared as described in Example 1.

Example 3

Slimming Cream for the Body

| A: | Acrylates/C$_{10-30}$ alkyl acrylate copolymer | 0.5% |
|---|---|---|
|  | Water | 12% |
| B: | Cyclohexasiloxane | 10% |
| C: | Triethanolamine | 4% |
|  | Water | 35% |
|  | Glyercol | 6% |
|  | Acefylline | 6% |
| D: | Polyacrylamide and C$_{13-14}$ isoparaffin and laureth-7 | 0.5% |
| E: | Water | qs |
|  | Hecogenin acetate | 4% |
|  | Alcohol | 15% |

The above cream may be prepared in the following manner. The polymer of phase A is dispersed in water at 40° C. with stirring. The constituents of phases C and E are dissolved at room temperature. Phase B is then introduced into phase A with rapid stirring. Next, phases C, D, and E are introduced with stirring into the mixture previously formed. The fineness of the emulsion is checked by microscope.

Example 4

Slimming Cream for the Face

| A: | Demineralized water | qs |
|---|---|---|
|  | Preserving agents | 0.25% |
|  | Carbomer | 0.4% |
|  | Glycerol | 3% |
|  | Caffeine | 2% |
| B1: | 20 EO oxyethylenated sorbitan stearate (polysorbate 60) | 0.9% |
| B2: | PEG-100 stearate and glyceryl stearate | 2.1% |
|  | Cetyl alcohol | 2.6% |
|  | Isononyl isononanoate | 11.5% |
|  | Octyldodecanol | 15% |
|  | Diosgenin | 0.5% |
|  | Butyl hydroxytoluene | 0.1% |
|  | UVB screening agent | 1% |
|  | Preserving agent | 0.15% |
| C: | Demineralized water | 2% |
|  | Triethanolamine | 0.3% |

The above composition may be prepared in the following manner. The constituents of phases A, B1, and B2 are separately brought to 70° C. with stirring. Phase C is prepared by mixing its constituents together at room temperature. Phase B1 is then added to phase B2, and the mixture of the two phases is then poured into phase A with rapid stirring. The mixture obtained is mixed for 10 minutes, after which phase C is introduced with stirring.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

What is claimed is:

1. A composition which comprises, in a physiologically acceptable medium:
   (A) at least one sapogenin selected from the group consisting of diosgenin, hecogenin, smilagenin, sarsapogenin, tigogenin, yamogenin, yuccagenin, a natural extract containing diosgenin, a natural extract containing hecogenin, a derivative of diosgenin, a derivative of hecogenin, and mixtures thereof; and
   (B) at least one xanthine base or a plant extract containing the same.

2. The composition according to claim 1, wherein said sapogenin is diosgenin.

3. The composition according to claim 1, wherein said sapogenin is a derivative of hecogenin.

4. The composition according to claim 3, wherein said derivative of hecogenin is hecogenin acetate.

5. The composition according to claim 1, wherein said natural extract is selected from the group consisting of extracts of wild yam rhizome and extracts of agave leaves.

6. The composition according to claim 1, wherein said sapogenin is present in said composition in an amount of from 0.001% to 10% by weight, of the total weight of said composition.

7. The composition according to claim 6, wherein said sapogenin is present in said composition in an amount of from 0.05% to 5% by weight, of the total weight of said composition.

8. The composition according to claim 1, wherein said xanthine base is selected from the group consisting of caffeine, theophylline, theobromine, acefylline, xanthinol nicotinate, diniprophylline, diprophylline, etamiphylline and its derivatives, etophylline, proxyphylline, pentophylline, propentophylline, pyridophylline, bamiphylline, and mixtures thereof.

9. The composition according to claim 8, wherein said xanthine base is selected from the group consisting of caffeine, theophylline, theobromine, acefylline, and mixtures thereof.

10. The composition according to claim 1, wherein said plant extract is selected from the group consisting of extracts of tea, extracts of coffee, extracts of guarana, extracts of Paraguay tea, extracts of cola, and mixtures thereof.

11. The composition according to claim 1, wherein said xanthine base is present in said composition in an amount of from 0.01% to 10% by weight, of the total weight of said composition.

12. The composition according to claim 11, wherein said xanthine base is present in said composition in an amount of from 0.1% to 7% by weight, of the total weight of said composition.

13. A method for combating cellulite, said method comprising applying to the skin, of a subject in need thereof, an effective amount of the composition of claim 1.

14. The method according to claim 13, wherein said sapogenin is selected from the group consisting of diosgenin, hecogenin, smilagenin, sarsapogenin, tigogenin, yamogenin, yuccagenin, and mixtures thereof.

15. The method according to claim 13, wherein said sapogenin is diosgenin.

16. The method according to claim 13, wherein said xanthine base is selected from the group consisting of caffeine, theophylline, theobromine, acefylline, and mixtures thereof.

17. A method for refining the figure or the contours of the face, said method comprising applying to the skin of the figure or the skin of the face, of a subject in need thereof, an effective amount of the composition of claim 1.

18. The method according to claim 17, wherein said sapogenin is selected from the group consisting of diosgenin, hecogenin, smilagenin, sarsapogenin, tigogenin, yamogenin, yuccagenin, and mixtures thereof.

19. The method according to claim 17, wherein said sapogenin is diosgenin.

20. The method according to claim 17, wherein said xanthine base is selected from the group consisting of caffeine, theophylline, theobromine, acefylline, and mixtures thereof.

21. The composition according to claim 1, wherein said xanthine base is caffeine.

22. The composition according to claim 2, wherein said xanthine base is caffeine.

23. The composition according to claim 4, wherein said xanthine base is caffeine.

24. The composition according to claim 12, wherein said xanthine base is caffeine.

25. The method according to claim 13, wherein said xanthine base is caffeine.

26. The method according to claim 15, wherein said xanthine base is caffeine.

27. The method according to claim 17, wherein said xanthine base is caffeine.

28. The method according to claim 19, wherein said xanthine base is caffeine.

29. The composition according to claim 1, wherein the xanthine base:sapogenin ratio is from 1.5:1 to 333:1.

30. The composition according to claim 1, wherein the xanthine base:sapogenin ratio is from 1.5:1 to 10:1.

31. The composition according to claim 1, wherein the xanthine base:sapogenin ratio is from 1.5:1 to 4:1.

32. The composition according to claim 1, wherein the xanthine base:sapogenin ratio is from 4:1 to 10:1.

33. The composition according to claim 22, wherein the xanthine base:sapogenin ratio is from 1.5:1 to 333:1.

34. The composition according to claim 22, wherein the xanthine base:sapogenin ratio is from 1.5:1 to 4:1.

35. The composition according to claim 1, wherein the sapogenin is selected from the group consisting of diosgenin, hecogenin, smilagenin, sarsapogenin, tigogenin, yamogenin, yuccagenin, a natural extract containing diosgenin, a natural extract containing hecogenin and mixtures thereof.

* * * * *